United States Patent [19]

Weiland

[11] Patent Number: 4,560,378
[45] Date of Patent: Dec. 24, 1985

[54] MEDICAL ACCESSORY

[76] Inventor: Mary C. Weiland, 13867 Aztec St., Sylmar, Calif. 91342

[21] Appl. No.: 529,368

[22] Filed: Sep. 6, 1983

[51] Int. Cl.$^4$ .......................... A61M 3/00; A61M 5/00
[52] U.S. Cl. ..................................... 604/83; 604/181; 604/187; 604/250; 604/256; 251/8
[58] Field of Search ............... 604/250, 256, 905, 280, 604/284, 240, 243, 56, 83, 118, 181, 187; 251/8

[56] References Cited

U.S. PATENT DOCUMENTS

| | | | |
|---|---|---|---|
| 3,513,849 | 5/1970 | Vaillancourt et al. | 604/256 |
| 3,741,217 | 6/1973 | Clarico | 604/256 |
| 3,800,799 | 4/1974 | McWhorter | 604/256 X |
| 4,036,232 | 7/1977 | Genese | 604/250 X |
| 4,312,493 | 1/1982 | Stauffer | 251/8 |

Primary Examiner—Stephen C. Pellegrino
Attorney, Agent, or Firm—Roger A. Marrs

[57] ABSTRACT

A medical device is disclosed herein for patient care in connection with syringe and catheter drainage and feeding procedures which includes an elongated, flexible extension tube having an adapted plug or fitting at each end and a control clamp operably carried along the length of tube. Each plug or fitting is provided with a pair of dissimilar sized connections adapted to insertably receive a plurality of sized syringe or catheter dispensing nozzles or tips. Caps are provided for covering the connections and a flexible clip is employed for releasably attaching the device to a support or to the clothing of an attending nurse or the patient himself.

1 Claim, 6 Drawing Figures

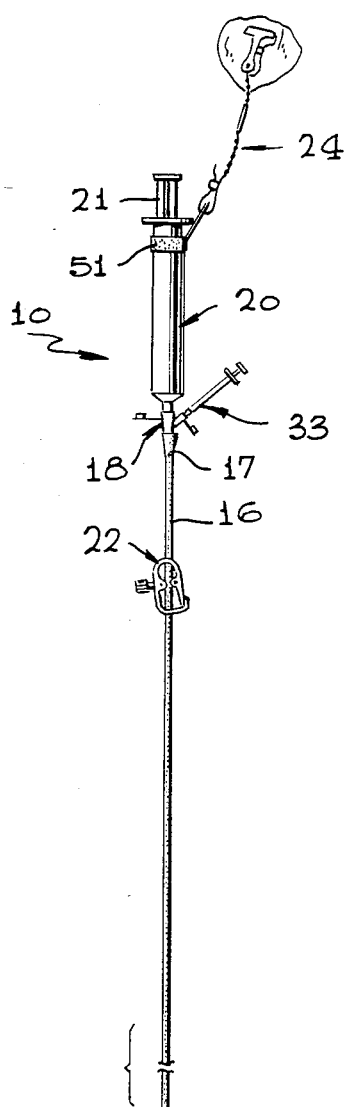
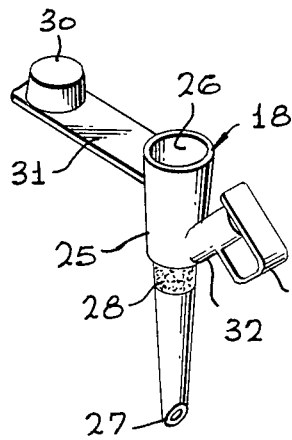
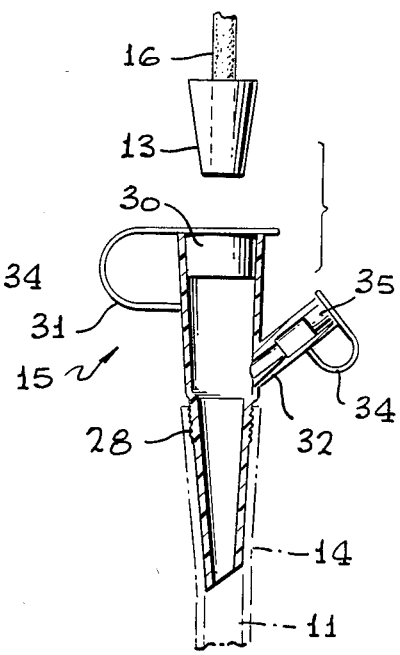
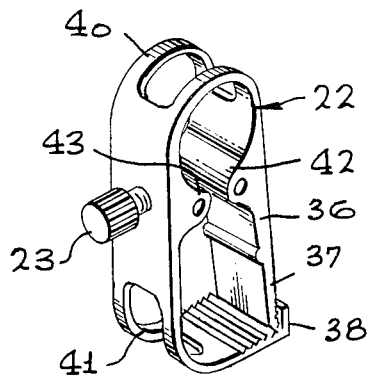
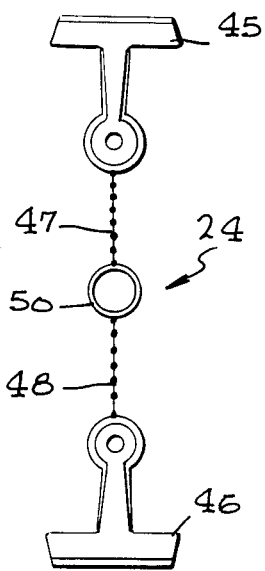
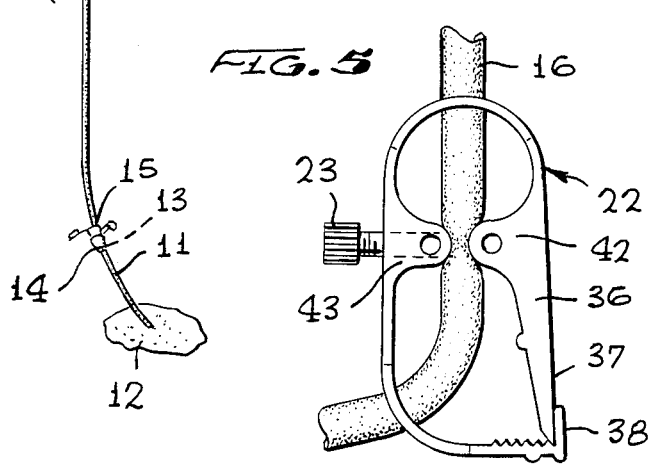

MEDICAL ACCESSORY

BACKGROUND OF THE INVENTION

1. Field of the Invention

The present invention relates to medical devices and accessories and, more particularly, to a novel dual inlet syringe adapter and a plug arrangement for use in patient feeding and drainage systems wherein greater freedom is permitted the patient and improved attendant management of the medical procedures results.

2. Brief Description of the Prior Art

In the past, it has been the conventional medical practice to perform patient feeding and drainage procedures by installing a feeding tube at one end into a patient and releasably securing a syringe to the other end of the tube. The attendant normally holds the syringe by hand and actuates the syringe plunger for forcing fluids out of the syringe through the tube into the patient or for extracting fluids from the patient by reversing the plunger of the syringe.

Problems and difficulties have been encountered when employing conventional medical devices for performing these procedures which stem largely from the fact that most catheters, drainage tubes, feeding tubes or the like very often permit the syringe or catheter to slip from engagement with the tube and this is particularly prevalent if the tubing is used frequently or for prolonged periods of time. Also, the attending nurse must hold the syringe onto the catheter or tubing during the entire procedure such as tube feeding, irrigation or specimen collection and must fumble with the remaining hand to manipulate the syringe and the plunger as well as the specimen or feeding container and associated solutions. Furthermore, should the patient desire to substantially move or walk about, the tube may be pulled out inadvertently or the catheter may become disconnected from the syringe.

Furthermore, in some instances such as for aspiration of fluids, the attending nurse cannot readily control the amount of suction when using the plunger of the syringe and, in some instances, the use of the plunger does not provide for a gentle, intermittent pressure to coax the gravity flow of fluid which is of great advantage in a procedure for aspiration of fluid.

Therefore, a long standing need has existed to provide a dual inlet syringe adapter and catheter for the administration of feeding and drainage procedures in connection with patient care which will stand constant or repeated use and which will continue to securely hold a syringe in place on tubing employed for feeding. Also, it is advantageous to provide such a medical aid which will permit the patient to be ambulatory and which includes adapters protecting the integrity of the patient's catheter so as to present it from becoming stretched or cracked and thereby minimizing the need to change the patient too frequently.

SUMMARY OF THE INVENTION

Accordingly, the above problems and difficulties are obviated by the present invention which provides a novel medical device employed in the practice of patient care which includes a feeding tube or normal length having an extension tube detachably connected between one end of the feeding tube and a syringe. The extension tube is elongated and flexible having an adapater plug or fitting at each end and a control clamp means operably carried along the length of the tube midway between its opposite ends. Each plug or fitting is formed with multiple receptacles or connection means adapted to insertably receive a plurality of different sized syringe tips and caps are integrally formed with the plugs for removably sealing the receptacles as desired. Attachment means are provided for supporting the medical device from a suitable support either stationary or the clothing of the attendant or the patient himself.

Therefore, it is among the primary objects of the present invention to provide a novel medical aid for use in patient care in connection with drainage or feeding procedures which will permit the patient reasonable mobility without inadvertent disconnection of syringes, catheters or the like.

Another object of the present invention is to provide a novel medical device which will withstand constant or repeated use and will maintain a syringe in place on tubing while the plunger is in operation.

Yet another object of the present invention is to provide a novel medical device having a dual inlet syringe adapter and catheter for use in connection with drainage and feeding procedures and which includes an extension tube interconnecting a pair of plugs at each end adapted to receive a variety of different sized syringe tips or nozzles.

Still a further object of the present invention is to provide a novel medical device having dual inlet connection plugs on oppostie ends of an extension cord adapted to removably engage with a feeding tube at one end and a syringe or the like at the opposite end.

BRIEF DESCRIPTION OF THE DRAWINGS

The features of the present invention which are believed to be novel are set forth with particularity in the appended claims. The present invention, both as to its organization and manner of operation, together with further objects and advantages whereof, may best be understood by reference to the following description taken in connection with the accompanying drawings in which:

FIG. 1 is a side elevational view of the novel medical device incorporating the present invention;

FIG. 2 is an enlarged perspective view of a novel dual inlet plug used in the device of FIG. 1;

FIG. 3 is longitudinal cross-sectional view of the dual inlet plug shown in FIG. 2;

FIG. 4 is a perspective view of a control clamp used in the device of FIG. 1;

FIG. 5 is a side elevational view of the control clamp shown in FIG. 4; and

FIG. 6 is a front elevational view of a clamping means used for supporting the medical device shown in FIG. 1.

DESCRIPTION OF THE PREFERRED EMBODIMENT

Referring to FIG. 1, the novel medical accessory of the present invention is indicated in the general direction of arrow 10 which includes a conventional feeding tube 11 which is connected at one end to a patient 12 by means of a suitable indwelling catheter means and which includes an enlarged opening 14 at its opposite end intended to receive a tapered plug connector 15 carried on one end of an extension tube 16 via a conical adapter 13. The opposite end of the extension tube from its end carrying adapter 13 terminates in a tapered opening 17 adapted to insertably receive a plug 18 similar to the plug 15. Insertably received into the plug 18 is the dispensing nozzle or tip of a syringe 20 which carries a fluid, for example, intended to be introduced to the patient 12 by displacement of a plunger 21. Although a syringe for feeding purposes is illustrated, it is to be understood that the syringe may also be used for drainage purposes and other medical procedures besides feeding.

The extension tube 16 includes a control clamp 22 which is of a snap-lock variety and which includes a rotating screw 23 adapted to controllably compress the tubing 16 so as to restrict the flow of fluid therethrough. Furthermore, the entire device 10 may be suitably supported from the clothing of the attending nurse, the clothing of the patient or from a stationary stand or support by means of a clip device indicated by numeral 24. Preferably, the device is flexible and is of sufficient length to accommodate the procedure being performed. By this means, the attending nurse has both hands available to assist or aid the patient or the procedure.

Referring now in detail to FIG. 2, the plug 18 includes an elongated, hollow body 25 open at one end to define an enlarged entrance 26 while terminating in a graduated taper defining a tip 27. Preferably, knurled or an irregular surface 28 is carried on the external surface of the tapered tip 27 so as to frictionally engage with the opening 17 on the extension tube 16. Such construction provides for a suitable joint which will not come apart easily. The plug 18 further includes a cap or lid 30 which is carried on one end of a strap 31 so that when the syringe 20 is not employed, the opening or entrance 26 may be closed, sealed and maintained ari tight. A feature of the plug 18 includes a lateral portion or body 32 which includes an internal passageway communicating with the hollow passageway of the body 25. Preferably, the portion or lateral body 32 is disposed in an angular relationship to the central longitudinal axis of the plug, as shown more clearly in FIG. 3, and the portion or body 32 is intended to receive a syringe such as identified by numeral 33 in FIG. 1. By this construction, a mixing of fluids or an injection of fluids at different times can be performed at different intervals without having to remove syringe 20. For example, medications may be introduced to the patient via the syringe 33 while the syringe 20 is being employed for feeding purposes. In a similar fashion to the closing of entrance 26, the portion or lateral body 32 includes a strap 34 having a closure element 35 on the end thereof adapted to seal, close and maintain airtight integrity.

As shown in FIG. 3, the flexible tubing 16 terminates in the tapered adapter 13 for connection with plug 15. The opening 14 insertably receives the tip 27 of the plug 15. The irregular surface 28 is gripped by the inner surface of the pliable tube opening 14. When the plugs 15 and 18 are not in use, the caps 30 and 35 are inserted into the openings of the respective bodies 25 and 32 so that sealing occurs. It is to be particularly noted that the internal passageway of the lateral body 32 is stepped in diameter by a series of shoulders so that a plurality of different sized syringe tips from the syringe 33 may be readily accommodated.

Referring now in detail to FIG. 4, the control clamp 22 is illustrated which includes a strap-like body 36 folded over upon itself and terminating in a hook arrangement at its opposite ends as indicated by numerals 37 and 38. The strap-like body 36 includes a pair of openings defined by side portions and broadly indicated by numerals 40 and 41 which pass a length of the extension tube 16 therethrough. The tube portion extending through the clamping device passes between thickened portions 42 and 43 so that these portions may press against the opposite sides of the tube and reduce the passageway therethrough so as to restrict the passage of fluid. Control is provided by snapping the extreme end of the terminating end 37 into ridges or grooves provided in the opposing end 38 of the strap-like body. The control screw 23 is threadably passed through the thickened portion 43 so that the end of the screw presses against the tube 16.

As shown more clearly in FIG. 5, the screw 23 passes through the thickened portion 43 and the nub or end thereof presses against the tube 16 forcing collapse or partial collapse of the tube against thickened portion 42 opposed to the portion 43. Also, resistance is provided by the hook arangement of the ends 37, 38. Therefore, control of fluid passing through the tubing 16 is achieved by adjustment of the screw 23.

Referring now to FIG. 6, the clip supporting means 24 is illustrated having upper and lower spring clips 45 and 46 connected together by means of chains 47 and 48 connected in common to a ring 50. It is to be understood that other forms of clip fasteners and holders may be provided. Preferably, clip 46 may be attached to the syringe by a band such as Velcro or, any form of snap or plastic bead and hole, such as in a buckle means may be provided. Such an arrangement is indicated by numeral 51 in FIG. 1.

With the feeding tube system of the present invention, the attending nurse and the patient have many options. Selected solutions or liquids can remain in the syringe with the extension tube clamped by the control means. With the syringe holder and clip assembly 24, the syringe may be suspended from an I.V. pole at any level or the syringe may be clipped to the collar of the nurse's uniform so as to allow her free use of both hands to assist the patient into a chair or to ambulate to a restroom. The syringe may even be suspended temporarily from the bed rail, light fixture or nearby curtain. The extension tubing 16 allows for added maneuverability and freedom of movement in and around the bed.

A feature of the invention also resides in a provision that a bulb syringe may be employed instead of a plunger 21. In this instance, the nurse can more readily control the amount of suction such as for aspiration of fluids or provide a gentle intermittent pressure to coax the gravity flow of fluids. The bulb syringe has the added advantage of not having to disconnect the syringe from the tubing 16. Used in conjunction with the extension tube 16 such as during a tube feeding, a check for residual can be made by first compressing the bulb syringe, then inserting it into the top of the syringe and allowing the bulb to reinflate. To remove a specimen, the procedure is the same but after the fluid is collected in the syringe, the tubing 16 is clamped by the clamping means 22 and the fluid can be poured out of the syringe.

By employing the dual inlet syringe plugs or adapters 18, not only can the syringe or catheter be connected to the tubing 16 but a second syringe can also be accommodated.

Therefore, it can be seen that the medical accessory of the present invention provides a novel device for improving patient care. Not only does the use of the extension tube 16 provide mobility for the patient, but the use of the dual inlet plug permits dual feeding or application of fluid to the patient. This is achieved under the control of the clamping means 22 and complete support of the device is provided by clamping means or suspension means 24.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. In a medical apparatus for use in performing medical procedures of an open system type employing an elongated, pliable patient in-place feeding or drainage tube, the combination comprising:

a syringe having a dispensing tip;

a pliable extension tube having one end detachably coupled with said syringe dispensing tip and its opposite end detachably coupled to said patient in-place tube;

fluid control means operably carried on said extension tube operable to selectively restrict the flow of fluid therethrough;

plug means disposed between said syringe tip and one end of said extension tube for mixing at least two fluids together;

said plug means comprising a hollow body terminating in a tapered portion adapted to be coupled with said extension tube and having a first entrance adapted to receive said syringe tip;

said plug body further provided with a laterally extending body having a tapered base having a second entrance for receiving a selected one of a plurality of syringe tips;

said plug means including closure means carried on said body and said lateral body for selectively sealing said bodies in the absence of syringe connections;

clip means operably carried on said syringe for releasably supporting said apparatus from supporting material or structure; and said fluid control means includes a rotary valve threadably carried on a strap-like body movably mounted on said extension tube for selectively closing said extension tube to restrict fluid flow therethrough.

* * * * *